United States Patent [19]

Dawson et al.

[11] Patent Number: 4,518,609
[45] Date of Patent: May 21, 1985

[54] NAPHTENIC AND HETEROCYCLIC RETINOIC ACID ANALOGUES

[75] Inventors: Marcia I. Dawson, Los Altos; Rebecca L. S. Chan, Palo Alto, both of Calif.

[73] Assignee: SRI International, Menlo Park, Calif.

[21] Appl. No.: 599,665

[22] Filed: Apr. 12, 1984

Related U.S. Application Data

[62] Division of Ser. No. 434,622, Oct. 15, 1982, Pat. No. 4,456,618.

[51] Int. Cl.³ .................... A61K 31/38; A61K 31/34
[52] U.S. Cl. .................... 514/448; 514/443; 549/57; 549/71; 549/72; 549/467; 549/468; 549/484; 549/487; 514/461; 514/469; 514/471
[58] Field of Search .............. 424/275, 285; 549/57, 549/71, 72, 467, 468, 484, 487

[56] References Cited

U.S. PATENT DOCUMENTS 4,456,618 6/1984 Dawson et al. .................... 424/308

OTHER PUBLICATIONS

Boutwell et al., Advances in Enzyme Regulation, vol. 17, (1979), pp. 89–112.
Verma et al., Cancer Res., vol. 39, (1979), pp. 419–427.
Dawson et al., J. Med. Chem., vol. 23, (1980), pp. 1013–1022.
Dawson et al., J. Med. Chem., vol. 24, (1981), pp. 583–592.

Primary Examiner—Alan Siegel
Attorney, Agent, or Firm—Ciotti & Murashige

[57] ABSTRACT

Naphthenic and heterocyclic retinoic acid analogues such as (E)-6-[2-(2,6,6-trimethyl-1-cyclohexen-1-yl)ethenyl]-2-naphthaldehyde, methyl 6-[2-(2,6,6-trimethyl-1-cyclohexen-1-yl)ethenyl]-2-naphthoate, 6-[2-(2,6,6-trimethyl-1-cyclohexen-1-yl)ethenyl]-2-naphthoic acid, (E)-1-(5-carbethoxy-2-furanyl)-2-methyl-4-(2,6,6-trimethyl-1-cyclohexen-1-yl)-1,3-butadiene, (E)-1-(5-carboxy-2-furanyl)-2-methyl-4-(2,6,6-trimethyl-1-cyclohexen-1-yl)-1,3-butadiene, (E)-1-(5-carbethoxythien-2-yl)-2-methyl-4-(2,6,6-trimethyl-1-cyclohexen-1-yl)-1,3-butadiene, and (E)-1-(5-carboxythien-2-yl)-2-methyl-4-(2,6,6-trimethyl-1-cyclohexen-1-yl)-1,3-butadiene. These retinoids are useful as chemopreventive agents for inhibiting tumor promotion in epithelial cells and for treating nonmalignant skin disorders.

20 Claims, No Drawings

NAPHTENIC AND HETEROCYCLIC RETINOIC ACID ANALOGUES

REFERENCE TO GOVERNMENT GRANT OR CONTRACT

The invention described herein was made in the course of work under grant or contract from the National Institute of Health.

This application is a division, of application Ser. No. 434,622, filed 15 Oct., 1982 now U.S. Pat. No. 4,456,618.

DESCRIPTION

1. Technical Field

The invention is in the fields of retinoid chemistry and chemotherapy. More particularly, the invention relates to certain naphthenic and heterocyclic retinoic acid analogues.

2. Background Art

The progressive loss of the regulation of cellular differentiation by epithelial cells can result in cancer. Retinoic acid and some of its analogues (retinoids) have been investigated as "chemopreventive" agents, that is, agents that interfere with tumor promotion in epithelial cells. Boutwell, et al; *Advances in Enzyme Regulation* V.17, Ed. Weber, G., Pergamon Press (1979); Verma, A. K., et al, *Cancer Res* (1979) 39:419–427; Dawson, M. I., et al, *J Med Chem* (1980) 23:1013–1022 and *J Med Chem* (1981) 24:583–592.

The latter Dawson, M. I., et al, article reports the preparation of (1E, 3E)- and (1Z, 3E)-1-(4-carboxyphenyl)-2-methyl-4-(2,6,6-trimethyl-1-cyclohexen-1-yl)-1,3-butadiene, the methyl and ethyl esters thereof, (E)-1-(2-carboxyphenyl)-4-methyl-6-(2,6,6-trimethyl-1-cyclohexen-1-yl)-1,3,5-hexatriene and the methyl ester thereof, (E)-1-[2-(tetrahydropyranyloxy)phenyl]-4-methyl-6(2,6,6-trimethyl-1-cyclohexen-1-yl)-1,3,5-hexatriene and the (1E, 3Z, 5E) isomer thereof, and (E)-1-(2-hydroxyphenyl)-4-methyl-6-(2,6,6-trimethyl-1-cyclohexen-1-yl)-1,3,5-hexatriene and its (1E, 3Z, 5E) isomer. Some of these mononuclear aromatic retinoic acid analogues exhibited biological activity in the ornithine decarboxylase (ODC) assay, which assay is described by Verma, A. K. and Boutwell, R. K., *Cancer Res* (1977) 37:2196–2201.

A principal object of this invention is to provide new naphthenic and heterocyclic retinoic acid analogues that are biologically active.

DISCLOSURE OF THE INVENTION

The retinoic acid analogues of the invention are of the formula

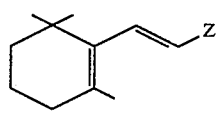
(1)

where Z is

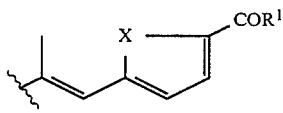

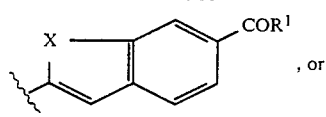, or

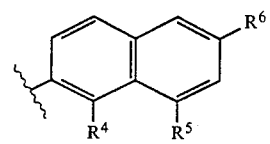

and X is a chalcogen atom of atomic number 8 or 16 (O or S), $R^1$ is hydroxyl, alkoxy, aroxy, or $NR^2R^3$ where $R^2$ is hydrogen, alkyl, or aryl and $R^3$ is alkyl or aryl, $R^4$ and $R^5$ are independently hydrogen, fluorine, methyl, or methoxy, and $R^6$ is

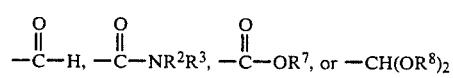

where $R^2$ and $R^3$ are as defined previously, $R^7$ is hydrogen, alkyl or aryl, and $R^8$ is alkyl or aryl.

When used as pharmaceuticals, eg, as a chemopreventive agent or for treating skin disorders such as proliferative skin diseases or acne, one or more of these retinoids is combined with a suitable pharmaceutically acceptable carrier and an effective dose thereof is administered to the patient.

Modes for Carrying Out the Invention

The alkoxy groups represented by $R^1$ will usually contain 1 to about 8 carbon atoms, preferably 1 to 4 carbon atoms, and the aroxy groups represented thereby will usually be mononuclear and contain 6 to 15 carbon atoms, more usually 6 to 10 carbon atoms. Preferred aroxy groups are phenoxy and hydroxy- or $C_1$–$C_4$ alkoxy-monosubstituted phenoxy. The alkoxy groups may be straight chain or branched chain. Examples of such alkoxy groups are methoxy, ethoxy, n-propoxy, i-propoxy, n-butoxy, s-butoxy, t-butoxy, n-pentoxy, n-hexoxy, 2-methylpentoxy, n-heptoxy, 3-methylhexoxy, and n-octoxy. Examples of aroxy groups are phenoxy, o-, m-, p-hydroxyphenoxy o-, m-, p-methoxyphenoxy, toloxy, cumoxy, xyloxy, and naphthoxy.

The alkyl groups represented by $R^2$ and $R^3$ may be straight chain or branched chain. They will typically each contain 1 to 8 carbon atoms, preferably 1 to 4 carbon atoms, and have 0 or 1 hydroxy substituent. Examples of such alkyl groups are methyl, ethyl, propyl, isopropyl, n-butyl, sec-butyl, n-amyl, n-hexyl, 2-methylamyl, n-heptyl, 3-methylhexyl, n-octyl, hydroxymethyl, 2-hydroxyethyl, 3-hydroxypropyl, 2-hydroxyhexyl, and the like. The corresponding aryl groups represented by $R^2$ and/or $R^3$ may be substituted or unsubstituted mononuclear or polynuclear moieties. The substituents will usually be lower (ie, 1 to 4 carbon atoms) alkyl, lower alkoxy, or hydroxy. When substituted, the group will usually be mono-substituted. Examples of such groups are phenyl, o-, m-, or p-hydroxyphenyl, o-, m-, or p-methoxyphenyl, ethylbenzyl, cumyl, naphthyl, phenanthryl, azulyl, and the like. These aryl groups will usually contain 6 to about 15 carbon atoms, more usually 6 to 10 carbon atoms. Phenyl, 4- hydroxyphenyl, and 4-methoxyphenyl are preferred aryl groups.

The alkyl groups represented by $R^7$ and $R^8$ will usually contain 1 to about 8 carbon atoms, preferably 1 to 4 carbon atoms, and the aryl groups represented thereby will usually be mononuclear and contain 6 to 15 carbon atoms, more usually 6 to 10 carbon atoms. Preferred aryl groups are phenyl and hydroxy- or $C_1$-$C_4$alkoxy-monosubstituted phenyl. The alkyl groups may be straight chain or branched chain. Examples of such alkyl groups are methyl, ethyl, n-propyl, i-propyl, n-butyl, s-butyl, t-butyl, n-amyl, n-hexyl, 2-methylamyl, n-heptyl, 3-methylhexyl, and n-octyl. Examples of aryl groups are phenyl, o-, m-, p-hydroxyphenyl, o-, m-, p-methoxyphenyl, tolyl, cumyl, xylyl, and naphthyl.

Examples of naphthenic retinoids represented by formula (1) are 6-[2-(2,6,6-trimethyl-1-cyclohexen-1-yl)ethenyl]-2-naphthoic acid, 4-fluoro-6-[2-(2,6,6-trimethyl-1-cyclohexen-1-yl)ethenyl]-2-naphthoic acid, 5-fluoro-6-[2-(2,6,6-trimethyl-1-cyclohexen-1-yl)-ethenyl]-2-naphthoic acid, 4-methoxy-6-[2-(2,6,6-trimethyl-1-cyclohexen-1-yl)ethenyl]-2-naphthoic acid, 5-methyl-6-[2-(2,6,6-trimethyl-1-cyclohexen-1-yl)-ethenyl]-2-naphthoic acid, methyl 6-[2-(2,6,6-trimethyl-1-cyclohexen-1-yl)ethenyl]-2-naphthoate, methyl 4-fluoro-6-[2-(2,6,6-trimethyl-1-cyclohexen-1-yl)ethenyl]-2-naphthoate, ethyl 4-methoxy-6-[2-(2,6,6-trimethyl-1-cyclohexen-1-yl)ethenyl]-2-naphthoate, butyl 6-[2-(2,6,6-trimethyl-1-cyclohexen-1-yl)-ethenyl]-2-naphthoate, heptyl 6-[2-(2,6,6-trimethyl-1-cyclohexen-1-yl)ethenyl]-2-naphthoate, octyl 6-[2-(2,6,6-trimethyl-1-cyclohexen-1-yl)ethenyl]-2-naphthoate, hexyl 4-methyl-6-[2-(2,6,6-trimethyl-1-cyclohexen-1-yl)ethenyl]-2-naphthoate, isopropyl 4,5-dimethoxy-6-[2-(2,6,6-trimethyl-1-cyclohexen-1-yl)ethenyl]-2-naphthoate, amyl 5-fluoro-6-[2-(2,6,6-trimethyl-1-cyclohexen-1-yl)ethenyl]-2-naphthoate, N-methyl-6-[2-(2,6,6-trimethyl-1-cyclohexen-1-yl)ethenyl]-2-naphthamide, N-2-hydroxyethyl-6-[2-(2,6,6-trimethyl-1-cyclohexen-1-yl)ethenyl]-2-naphthamide, N-4-hydroxyphenyl-6-[2-(2,6,6-trimethyl-1-cyclohexen-1-yl)ethenyl]-2-naphthamide, N-4-methoxyphenyl-6-[2-(2,6,6-trimethyl-1-cyclohexen-1-yl)ethenyl]-2-naphthamide, N,N-dimethyl-6-[2-(2,6,6-trimethyl-1-cyclohexen-1-yl)ethenyl]-2-naphthamide, N-phenyl-6-[2-(2,6,6-trimethyl-1-cyclohexen-1-yl)ethenyl]-2-naphthamide, N-2-hydroxyethyl 4-fluoro-6-[2-(2,6,6-trimethyl-1-cyclohexen-1-yl)ethenyl]-2-naphthamide, N-4-hydroxyphenyl-4,5-difluoro-6-[2-(2,6,6-trimethyl-1-cyclohexen-1-yl)ethenyl]-2-naphthamide, N-octyl-6-[2-(2,6,6-trimethyl-1-cyclohexen-1-yl)ethenyl]-2-naphthamide, 6-[2-(2,6,6-trimethyl-1-cyclohexen-1-yl)ethenyl]-2-naphthaldehyde, 4-fluoro-6-[2,6,6-trimethyl-1-cyclohexen-1-yl)ethenyl]-2-naphthaldehyde, 4-methoxy-6-[2-(2,6,6-trimethyl-1-cyclohexen-1-yl)ethenyl]-2-naphthaldehyde, 4,5-dimethyl-6-[2-(2,6,6-trimethyl-1-cyclohexen-1-yl)ethenyl]-2-naphthaldehyde, phenyl 6-[2-(2,6,6-trimethyl-1-cyclohexen-1-yl)ethenyl]-2-naphthoate, phenyl 4-fluoro-6-[2-(2,6,6-trimethyl-1-cyclohexen-1-yl)ethenyl]-2-naphthoate, p-hydroxyphenyl 6-[2-(2,6,6-trimethyl-1-cyclohexen-1-yl)ethenyl]-2-naphthoate, tolyl 6-[2-(2,6,6-trimethyl-1-cyclohexen-1-yl)ethenyl]-2-naphthoate, and 6-[2-(2,6,6-trimethyl-1-cyclohexen-1-yl)ethenyl]-2-naphthaldehydediethylacetal.

Examples of heterocyclic retinoids represented by formula (1) are (E)-1-(5-carboxy-2-furanyl)-2-methyl-4-(2,6,6-trimethyl-1-cyclohexen-1-yl)-1,3-butadiene, (E)-1-(5-carbmethoxy-2-furanyl)-2-methyl-4-(2,6,6-trimethyl-1-cyclohexen-1-yl)-1,3-butadiene, (E)-1-(5-carbethoxy-2-furanyl)-2-methyl-4-(2,6,6-trimethyl-1-cyclohexen-1-yl)-1,3-butadiene, (E)-1-(5-carboxy-2-furanyl)-2-methyl-4-(2,6,6-trimethyl-1-cyclohexen-1-yl)-1,3-butadiene, (E)-1-(5-carbisopropoxy-2-furanyl)-2-methyl-4-(2,6,6-trimethyl-1-cyclohexen-1-yl)-1,3-butadiene, (E)-1-(5-carbbutoxy-2-furanyl)-2-methyl-4-(2,6,6-trimethyl-1-cyclohexen-1-yl)-1,3-butadiene, (E)-1-(5-carbhexoxy-2-furanyl)-2-methyl-4-(2,6,6-trimethyl-1-cyclohexen-1-yl)-1,3-butadiene, (E)-1-(5-carbheptoxy-2-furanyl)-2-methyl-4-(2,6,6-trimethyl-1-cyclohexen-1-yl)-1,3-butadiene, (E)-1-(5-carboctoxy-2-furanyl)-2-methyl-4-(2,6,6-trimethyl-1-cyclohexen-1-yl)-1,3-butadiene, (E)-1-(5-carbphenoxy-2-furanyl)-2-methyl-4-(2,6,6-trimethyl-1-cyclohexen-1-yl)-1,3-butadiene, (E)-1-(5-carb-p-hydroxyphenoxy-2-furanyl)-2-methyl-4-(2,6,6-trimethyl-1-cyclohexen-1-yl)-1,3-butadiene, (E)-1-(5-methylcarbamoyl-2-furanyl)-2-methyl-4-(2,6,6-trimethyl-1-cyclohexen-1-yl)-1,3-butadiene, (E)-1-(5-hexylcarbamoyl-2-furanyl)-2-methyl-4-(2,6,6-trimethyl-1-cyclohexen-1-yl)-1,3-butadiene, (E)-1-(5-2'-hydroxyethylcarbamoyl-2-furanyl)-2-methyl-4-(2,6,6-trimethyl-1-cyclohexen-1-yl)-1,3-butadiene, (E)-1-(5-4'-hydroxyphenylcarbamoyl-2-furanyl)-2-methyl-4-(2,6,6-trimethyl-1-cyclohexen-1-yl)-1,3-butadiene, (E)-1-(5-4'-methoxyphenylcarbamoyl-2-furanyl)-2-methyl-4-(2,6,6-trimethyl-1-cyclohexen-1-yl)-1,3-butadiene, (E)-1-(5-dimethylcarbamoyl-2-furanyl)-2-methyl-4-(2,6,6-trimethyl-1-cyclohexen-1-yl)-1,3-butadiene, (E)-1-(5-phenylcarbamoyl-2-furanyl)-2-methyl-4-(2,6,6-trimethyl-1-cyclohexen-1-yl)-1,3-butadiene, (E)-1-(5-methylphenylcarbamoyl-2-furanyl)-2-methyl-4-(2,6,6-trimethyl-1-cyclohexen-1-yl)-1,3-butadiene, (E)-1-(5-octylcarbamoyl-2-furanyl)-2-methyl-4-(2,6,6-trimethyl-1-cyclohexen-1-yl)-1,3-butadiene, (E)-1-(5-carboxythien-2-yl)-2-methyl-4(2,6,6-trimethyl-1-cyclohexen-1-yl)-1,3-butadiene, (E)-1-(5-carbmethoxythien-2-yl)-2-methyl-4-(2,6,6-trimethyl-1-cyclohexen-1-yl)-1,3-butadiene, (E)-1-(5-carbethoxythien-2-yl)-2-methyl-4-(2,6,6-trimethyl-1-cyclohexen-1-yl)-1,3-butadiene, (E)-1-(5-carbpropoxythien-2-yl)-2-methyl-4-(2,6,6-trimethyl-1-cyclohexen-1-yl)-1,3-butadiene, (E)-1-(5-carbpentoxythien-2-yl)-2-methyl-4-(2,6,6-trimethyl-1-cyclohexen-1-yl)-1,3-butadiene, (E)-1-(5-carboctoxythien-2-yl)-2-methyl-4-(2,6,6-trimethyl-1-cyclohexen-1-yl)-1,3-butadiene, (E)-1-(5-carbphenoxythien-2-yl)-2-methyl-4-(2,6,6-trimethyl-1-cyclohexen-1-yl)-1,3-butadiene, (E)-1-(5-carbamoylthien-2-yl)-2-methyl-4-(2,6,6-trimethyl-1-cyclohexen-1-yl)-1,3-butadiene, (E)-1-(5-isopropylcarbamoylthien-2-yl)-2-methyl-4-(2,6,6-trimethyl-1-cyclohexen-1-yl)-1,3-butadiene, (E)-1-(5-ethylmethylcarbamoylthien-2-yl)-2-methyl-4-(2,6,6-trimethyl-1-cyclohexen-1-yl)-1,3-butadiene, (E)-1-(5-heptylcarbamoylthien-2-yl)-2-methyl-4-(2,6,6-trimethyl-1-cyclohexen-1-yl)-1,3-butadiene, (E)-1-(5-octylcarbamoylthien-2-yl)-2-methyl-4-(2,6,6-trimethyl-1-cyclohexen-1-yl)-1,3-butadiene, (E)-1-(5-hydroxymethylcarbamoylthien-2-yl)-2-methyl-4-(2,6,6-trimethyl-1-cyclohexen-1-yl)-1,3-butadiene, (E)-1-(5-2'-hydroxyethylcarbamoylthien-2-yl)-2-methyl-4-(2,6,6-trimethyl-1-cyclohexen-1-yl)-1,3-butadiene, (E)-1-(5-4'-hydroxyphenylcarbamoylthien-2-yl)-2-methyl-4-(2,6,6-trimethyl-1-cyclohexen-1-yl)-1,3-butadiene, (E)-1-(5-4'-methoxyphenylcarbamoylthien-2-yl)-2-methyl-4-(2,6,6-trimethyl-1-cyclohexen-1-yl)-1,3-butadiene, (E)-1-(5-4'-butoxyphenylthien-2-yl)-2-methyl-4-(2,6,6-trimethyl-1-cyclohexen-1-yl)-1,3-butadiene, (E)-1-(5-phenylcarbamoylthien-2-yl)-2-methyl-4-(2,6,6-trimethyl-1- cyclohexen-1-yl)-1,3-butadiene, (E)-1-(5-methylphenylcarbamoylthien-2-yl)-2-methyl-4-(2,6,6-trimethyl-1-cyclohexen-1-yl)-1,3-butadiene, (E)-1-(6-carboxy-2-benzofuranyl)-2-methyl-4-(2,6,6-trimethyl-1-cyclohexen-1-yl)-1,3-butadiene, (E)-1(6-carbethoxy-2-benzofuranyl)-2-methyl-4-(2,6,6-trimethyl-1-cyclohexen-1-yl)-1,3-butadiene, (E)-1-(6-carbbutoxy-2-benzofuranyl)-2-methyl-4-(2,6,6-trimethyl-1-cyclohexen-1-yl)-1,3-butadiene, (E)-1-(6-carbphenoxy-2-benzofuranyl)-2-methyl-4-(2,6,6-trimethyl-1-cyclohexen-1-yl)-1,3-butadiene, (E)-1-(6-methylcarbamoyl-2-benzofuranyl)-2-methyl-4-(2,6,6-trimethyl-1-cyclohexen-1-yl)-1,3-butadiene, (E)-1-(6-ethylcarbamoyl-2-benzofuranyl)-2-methyl-4-(2,6,6-trimethyl-1cyclohexen-1-yl)-1,3-butadiene, (E)-1-(6-amylcarbamoyl-2-benzofuranyl)-2-methyl-4-(2,6,6-trimethyl-1-cyclohexen-1-yl)-1,3-butadiene, (E)-1-(6-octylcarbamoyl-2-benzofuranyl)-2-methyl-4-(2,6,6-trimethyl-1-cyclohexen-1-yl)-1,3-butadiene, (E)-1-(6-methyloctylcarbamoyl-2-benzofuranyl)-2-methyl-4-(2,6,6-trimethyl-1-cyclohexen-1-yl)-1,3-butadiene, (E)-1-(6-phenylcarbamoyl-2-benzofuranyl)-2-methyl-4-(2,6,6-trimethyl-1-cyclohexen-1-yl)-1,3-butadiene, (E)-1-(6-naphthylcarbamoyl-2-benzofuranyl)-2-methyl-4-(2,6,6-trimethyl-1-cyclohexen-1-yl)-1,3-butadiene, (E)-1-(6-2'-hydroxyethylcarbamoyl-2-benzofuranyl)-2-methyl-4-(2,6,6-trimethyl-1-cyclohexen-1-yl)-1,3-butadiene, (E)-1-(6-4'-hydroxyphenylcarbamoyl-2-benzofuranyl)-2-methyl-4-(2,6,6-trimethyl-1-cyclohexen-1-yl)-1,3-butadiene, (E)-1-(6-4'-methoxyphenylcarbamoyl-2-benzofuranyl)-2-methyl-4-(2,6,6-trimethyl-1-cyclohexen-1-yl)-1,3-butadiene, (E)-1-(6-dimethylcarbamoyl-2-benzofuranyl)-2-methyl-4-(2,6,6-trimethyl-1-cyclohexen-1-yl)-1,3-butadiene, (E)-1-(6-carboxy-2-benzothiofuranyl)-2-methyl-4-(2,6,6-trimethyl-1-cyclohexen-1-yl)-1,3-butadiene, (E)-1-(6-carbmethoxy-2-benzothiofuranyl)-2-methyl-4-(2,6,6-trimethyl-1-cyclohexen1yl)-1,3-butadiene, (E)-1-(6-carbisopropoxy-2-benzothiofuranyl)-2-methyl-4-(2,6,6-trimethyl-1-cyclohexen-1-yl)-1,3-butadiene, (E)-1-(6-carboctoxy-2-benzothiofuranyl)-2-methyl-4-(2,6,6-trimethyl-1-cyclohexen-1-yl)-1,3-butadiene, (E)-1-(6-carb-p-hydroxyphenoxy-2-benzothiofuranyl)-2-methyl-4-(2,6,6-trimethyl-1-cyclohexen-1-yl)-1,3-butadiene, (E)-1-(6-methylcarbamoyl-2-benzothiofuranyl)-2-methyl-4-(2,6,6-trimethyl-1-cyclohexen-1-yl)-1,3-butadiene, (E)-1-(6-ethylcarbamoyl-2-benzothiofuranyl)-2-methyl-4-(2,6,6-trimethyl-1-cyclohexen-1-yl)-1,3-butadiene, (E)-1-(6-butylcarbamoyl-2-benzothiofuranyl)-2-methyl-4-(2,6,6-trimethyl-1-cyclohexen-1-yl)-1,3-butadiene, (E)-1-(6-octylcarbamoyl-2-benzothiofuranyl)-2-methyl-4-(2,6,6-trimethyl-1-cyclohexen-1-yl)-1,3-butadiene, (E)-1-(6-ethylmethylcarbamoyl-2-benzothiofuranyl)-2-methyl-4-(2,6,6-trimethyl-1-cyclohexen-1-yl)-1,3-butadiene, (E)-1-(6-methyloctylcarbamoyl-2-benzothiofuranyl)-2-methyl-4-(2,6,6-trimethyl-1-cyclohexen-1-yl)-1,3-butadiene, (E)-1-(6-diethylcarbamoyl-2-benzothiofuranyl)-2-methyl-4-(2,6,6-trimethyl-1-cyclohexen-1-yl)-1,3-butadiene, (E)-1-(6-2'-hydroxyethylcarbamoyl-2-benzothiofuranyl)-2-methyl-4-(2,6,6-trimethyl-1-cyclohexen-1-yl)-1,3-butadiene, (E)-1-(6-hydroxymethylcarbamoyl-2-benzothiofuranyl)-2-methyl-4-(2,6,6-trimethyl-1-cyclohexen-1-yl)-1,3-butadiene, (E)-1-(6-phenylcarbamoyl-2-benzothiofuranyl)-2-methyl-4-(2,6,6-trimethyl-1-cyclohexen-1-yl)-1,3-butadiene, (E)-1-(6-4'-hydroxyphenylcarbamoyl-2-benzothiofuranyl)-2-methyl-4-(2,6,6-trimethyl-1-cyclohexen-1-yl)-1,3-butadiene, (E)-1-(6-4'-methoxyphenylcarbamoyl-2-benzothiofuranyl)-2-methyl-4-(2,6,6-trimethyl-1-cyclohexen-1-yl)-1,3-butadiene, (E)-1-(6-naphthylcarbamoyl-2-benzothiofuranyl)-2-methyl-4-(2,6,6-trimethyl-1-cyclohexen-1-yl)-1,3-butadiene, (E)-1-(6-4'-butoxyphenylcarbamoyl-2-benzothiofuranyl)-2-methyl-4-(2,6,6-trimethyl-1-cyclohexen-1-yl)-1,3-butadiene, and (E)-1-(6-2'-hydroxyhexylcarbamoyl-2-benzothiofuranyl)-2-methyl-4-(2,6,6-trimethyl-1-cyclohexen-1-yl)-1,3-butadiene.

The retinoids of formula (1) may be prepared by reacting an appropriate aldehyde with β-cyclogeranyltriphenylphosphonium bromide in the case of the fused ring analogues of formula (1) or β-ionyl-triphenylphosphonium bromide in the case of the furan and thiofuran analogues of formula (1). These reactions are depicted below.

For fused ring analogues

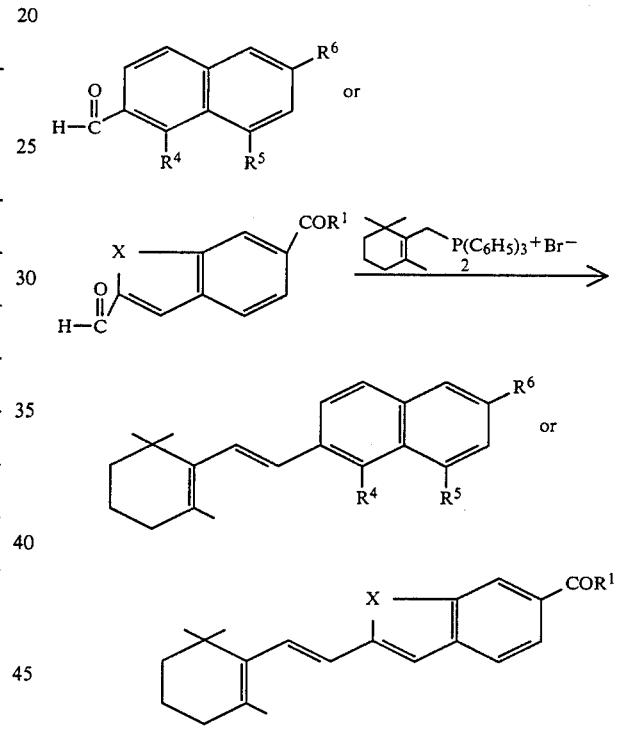

For furan and thiofuran analogues

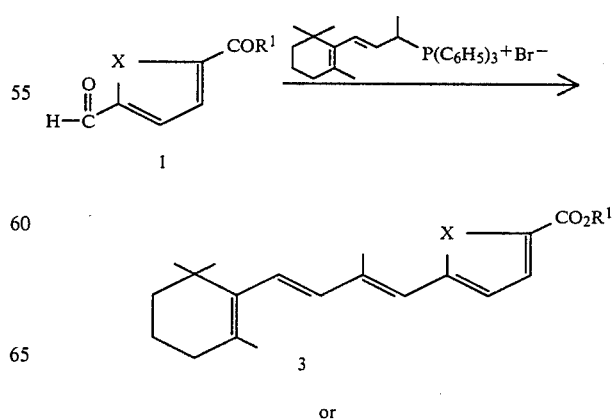

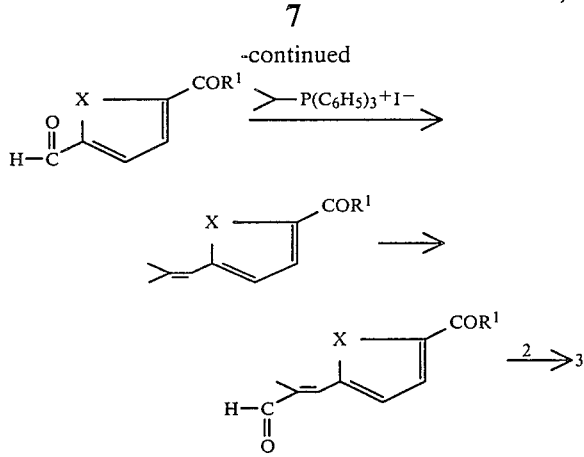

In those instances where the analogue is an acid ($R^1$ is hydroxyl or $R^6$ is carboxy) a corresponding ester is prepared and the ester is hydrolyzed to form the acid. The amides may be made from the acids.

The following examples further illustrate retinoic acid analogues of the invention and their preparation. These examples are not intended to limit the invention in any manner. The subscript R indicates use of the retinoid numbering system. The following abbreviations are used in these examples: THF=tetrahydrofuran; Bu=butyl; Et=ethyl, Ac=

LC=liquid chromatography; IR=infrared; NMR=nuclear magnetic resonance; UV=ultraviolet; LAH=lithium aluminum hydride; DMF=dimethyl formamide; TLC=thin layer chromatography; Me=methyl; HPLC=high-performance liquid chromatography.

EXAMPLE 1

Preparation of (E)-6-[2-(2,6,6-trimethyl-1-cyclohexen-1-yl)ethenyl]-2-naphthaldehyde.

A mixture of 2.74 g (14.7 mmol) of 2,6-napthalenedicarboxaldehyde and 7.00 g (14.6 mmol) of β-cyclogeranyltriphenylphosphonium bromide in 40 mL of dry THF and 5.5 mL of dry t-BuOH was stirred and cooled in a −20° C. bath. Then 1.65 g (14.7 mmol) of t-BuOK in 18 mL of t-BuOH was added over a period of 4 min. The resultant tannish orange mixture was stirred at ambient temperature for 21 h and then diluted with 200 mL of hexane and 100 mL of $H_2O$ containing 2 drops of HOAc. The aqueous layer was extracted with 100 mL of hexane. The organic extracts were washed with two 50-mL portions of $H_2O$ and brine, dried ($MgSO_4$), and concentrated at reduced pressure to a yellow oil and solid which—after extraction with 100-mL portions of hexane and 5% EtOAc/hexane—gave 5.7 g of yellow oil and some solid. This material was chromatographed on 300 g of silica gel. Elution with 600 mL of hexane followed by 5% EtOAc/hexane gave two fractions of 1.7 g and 1.4 g. The first fraction was rechromatographed on 100 g of silica gel eluted in the same manner to afford 0.7 g of yellow oil, which was combined with the second fraction. These combined fractions were purified by preparative LC with 3% EtOAc/hexane to give 1.89 g (42%) of viscous yellow oil, which solidified on cooling, mp 35°–37° C.

A similar sample was completely characterized: LC (Radialpak B, 5% EtOAc/hexane, 2 mL/min, 260 nm) $t_R$ 3.8 (0.5%), 4.0 (99%), 4.4 min (<0.5%); LC (Radialpak A, 10% $H_2O/CH_3CN$, 2 mL/min, 260 nm) $t_R$ 1.0 (1%), 6.8 (0.5%), 7.2 min (98%); IR (film) 2720, 1690 (C=O), 1620, 1575, 1120, 970, 890, 815 cm$^{-1}$; $^1$H NMR (CDCl$_3$) δ1.11 (s, 6, 16$_R$, 17$_R$ CH$_3$), 1.45–1.75 (m, 4, 2$_R$, 3$_R$ CH$_2$), 1.80 (d, J=0.5 Hz, 3, 18$_R$ CH$_3$), 2.08 (m, 2, 4$_R$ CH$_2$), 6.52 (s, J=16 Hz, 1, 8$_R$ HC=CH), 6.94 (d, J=16 Hz, 1, 7$_R$ HC=CH), 7.65–8.0 (m, 4, 3'H, 4'H, 5'H, 8'H), 7.75 (dd, J=2 Hz, J=10 Hz, 1, 7'H), 8.26 (broad s, 1, 1', H), 10.12 (s, 1, CHO); $^{13}$C NMR (CDCl$_3$) 19.2 (3$_R$), 21.8 (18$_R$), 29.0 (16$_R$, 17$_R$), 33.1 (4$_R$), 34.4 (1$_R$), 39.6 (2$_R$), 97.7, 123.3, 124.7, 125.3, 128.8, 129.6, 130.3, 130.6, 131.8 (5$_R$), 132.1, 133.7, 134.0, 136.9 (6$_R$), 138.9, 192.0 ppm (C=O); UV (EtOH) λ$_{max}$ 240 nm (ϵ3.03×10$^4$), 263 nm (ϵ2.23×10$^4$), 327 nm (ϵ2.36×10$^4$). MS calcd for C$_{22}$H$_{24}$O 304.1827, found 304.1846.

EXAMPLE 2

Preparation of methyl 6-[2-(2,6,6-trimethyl-1-cyclohexen-1-yl)ethenyl]-2-naphthoate:

2-Acetoxymethyl-6-hydroxymethylnaphthalene

A 2.4-g (12.8-mmol) portion of 2,6-dihydroxymethylnaphthalene, which had been prepared by reduction of 2,6-dicarbomethoxynaphthalene with LAH in refluxing THF, was refluxed with 50 mL of HOAc and 2 mL of $H_2O$ for 1.5 h. The reaction mixture was evaporated to dryness, dissolved in a minimum amount of EtOAc, and chromatographed on a 4.5×30-cm column of silica gel with 50% EtOAc/hexane. The diacetate (1.15 g, 33% yield) eluted first, followed by 1.45 g (49% yield) of the monoacetate. A portion of the monoacetate was recrystallized from EtOAc/hexane to give white crystals: mp 118°–119° C.; IR (mull) 3300, 1750, 1260, 1050, 910, 840, 740 cm$^{-1}$; $^1$H NMR (CDCl$_3$) δ2.08 (s, 3, CH$_3$), 2.87 (s, 1, OH), 4.75 (s, 2, CH$_2$OH), 5.22 (s, 2, CH$_2$OCOCH$_3$), 7.40 (d, J=8 Hz, 2, 4', 8'H), 7.72 (s, 2, 1', 5'H), 7.77 (d, J=8 Hz, 2, 3', 7'H); MS calcd for C$_{14}$H$_{14}$O$_3$ 230.0943, found 230.0915.

Methyl 6-Acetoxymethyl-2-naphthoate.

A mixture of 1.3 g (5.7 mmole) of the monoacetate and 20 g (57 mmol) of pyridinium dichromate in 20 mL of DMF was stirred at room temperature for 3 days. TLC (50% EtOAc/hexane) indicated only one product. The mixture was diluted with 200 mL of $H_2O$ and extracted with Et$_2$O (3×150 mL). The Et$_2$O layer was dried (Na$_2$SO$_4$) and concentrated to give 1.3 g (94% yield) of 6-acetoxymethyl-2-naphthoic acid as white crystals. Recrystallization from EtOAc gave almost colorless crystals: mp 225°–228° C.; IR (mull) 1740, 1700, 1300, 1240, 1210, 1030, 960, 920, 820, 760, 730 cm$^{-1}$; $^1$H NMR (CDCl$_3$/Me$_2$SO-d$_6$) δ2.12 (s, 3, CH$_3$), 5.28 (s, 2, CH$_2$), 7.5–8.7 (m, 6, ArH); MS calcd for C$_{14}$H$_{12}$O$_4$ 244.0746, found 244.0742.

To a suspension of 1.08 g (4.43 mmol) of 6-acetoxymethyl-2-naphthoic acid in 150 mL of Et$_2$O at 0° C. was added a cold solution of CH$_2$N$_2$ in Et$_2$O which was prepared from 2.0 g (19 mmol) of N-methyl-N-nitrosourea and 30 mL of 40% aqueous KOH. The mixture was stirred at 0° C. for 10 min when all the solid went into solution. Excess CH$_2$N$_2$ was decomposed with HOAc. The reaction mixture was dried over Na$_2$SO$_4$ and concentrated to give 1.6 g of a white solid, which was purified on 100 g of silica gel (50% EtOAc/hexane) to give 1.04 g (91% yield) of the pure methyl ester. A portion was recrystallized from EtOAc/hexane to give white plates: mp 115°–116° C.; IR (mull) 1720, 1300, 1260, 1200, 1140, 1100, 1040, 980, 940, 900, 840, 820, 760 cm$^{-1}$; $^1$H NMR (CDCl$_3$) δ2.15 (s, 3, CH$_3$CO$_2$), 3.98 (s, 3, CO$_2$CH$_3$), 5.28 (s, 2, CH$_2$O), 7.3–8.7 (m, 6, ArH); MS calcd for C$_{15}$H$_{14}$O$_4$ 258.0892, found 258.0872.

6-Carbomethoxy-2-naphthaldehyde

To a solution of 0.9 g (3.49 mmol) of methyl 6-acetoxymethyl-2-naphthoate in 100 mL of MeOH was added 0.5 g (3.62 mmol) of K$_2$CO$_3$ and 1 mL of H$_2$O. The mixture was stirred at room temperature for 30 min before being evaporated to dryness. The residue was taken up in 50 mL of EtOAc and 30 mL of H$_2$O. The organic layer was dried (Na$_2$SO$_4$) and evaporated to give 0.76 g (100% yield) of methyl 6-hydroxymethyl-2-naphthoate as white crystals: mp 123°–124° C.; IR (mull) 3250, 1720, 1300, 1200, 1130, 1100, 1040, 1020, 920, 900, 840, 820, 760 cm$^{-1}$; $^1$H NMR (CDCl$_3$) δ2.13 (s, 1, OH), 3.98 (s, 3, CO$_2$CH$_3$), 4.88 (s, 2, CH$_2$OH), 7.3–8.7 (m, 6, ArH); MS calcd for C$_{13}$H$_{12}$O$_3$ 216.0786, found 216.0787.

A mixture of 5 mL (61.8 mmol) of pyridine and 70 mL of CH$_2$Cl$_2$ was cooled to 0° C. Then 3.0 g (30 mmol) of CrO$_3$ was added in several portions. The mixture was stirred at 0° C. for 15 min before a solution of 0.69 g (3.19 mmol) of methyl 6-hydroxymethyl-2-naphthoate in 10 mL of CH$_2$Cl$_2$ was added. The mixture was stirred at room temperature for 2 hr and then filtered through Florisil (500 mL CH$_2$Cl$_2$ rinse). The filtrate and washings were concentrated and filtered through 50 g of silica gel with 50% EtOAc/hexane to give 0.66 g (96% yield) of the pure aldehyde as a white solid. The analytical sample was recrystallized from EtOAc/hexane: mp 132°–134° C.; IR (mull) 1740, 1700, 1350, 1310, 1270, 1220, 1180, 1140, 1110, 990, 920, 830, 780, 760 cm$^{-1}$; $^1$H NMR (CDCl$_3$) δ4.00 (s, 3, CO$_2$CH$_3$), 8.0–8.7 (m, 6, ArH), 10.23 (s, 1, CHO); MS calcd for C$_{13}$H$_{10}$O$_3$ 214.0630, found 214.0627.

Methyl 6-[2-[2,6,6-trimethyl-1-cyclohexen-1-yl)ethenyl]-2-naphthoate

To a suspension of 1.39 g (2.9 mmol) of β-cyclogeranyltriphenylphosphonium bromide in 40 mL of THF at −20° C. was added 1.88 mL of a 1.54M solution of n-BuLi (2.9 mmol) in hexane. The mixture was stirred for 20 min at 0° C., at which time almost all of the phosphonium salt went into solution. To the dark brown solution was added 0.62 g (2.9 mmol) of 6-carbomethoxy-2-naphthaldehyde in 5 mL of THF. The reaction mixture became light yellow. It was stirred at room temperature for 24 h and then diluted with 200 mL of H$_2$O and extracted with Et$_2$O (3×100 mL). The Et$_2$O layer was dried (Na$_2$SO$_4$), concentrated, and filtered through 100 g of silica gel to give 0.8 g (82% yield) of methyl 6-[2-(2,6,6-trimethyl-1-cyclohexen-1-yl)-2-naphthoate as a very pale yellow oil: IR (film) 2950, 1730, 1640, 1490, 1450, 1390, 1360, 1300, 1260, 1220, 1140, 1110, 1060, 980, 920, 900, 820, 780, 760 cm$^{-1}$; $^1$H NMR (CDCl$_3$) δ1.12 (s, 6, 16$_R$, 17$_R$ CH$_3$), 1.3–1.8 (m, 4, 2$_R$,3$_R$ CH$_2$), 1.82 (s, 3, 18$_R$ CH$_3$), 1.9–2.2 (m, 2, 4$_R$ CH$_2$), 3.97 (s, 3, CO$_2$CH$_3$), 6.52 (d, J=18 Hz, 8$_R$ C═CH), 6.95 (d, J=18 Hz, 7$_R$ HC═C), 7.7–8.7 (m, 6, ArH).

EXAMPLE 3

Preparation of 6-[2-(2,6,6-trimethyl-1-cyclohexen-1-yl)ethenyl]-2-naphthoic acid A suspension of 0.75 g (2.25 mmol) of methyl 6-[2-(2,6,6-trimethyl-1-cyclohexen-1-yl)ethenyl]-2-naphthoate in 5 mL of MeOH was degassed twice. A solution of 1 g (17.8 mmol) of KOH in 2 mL of H$_2$O and 3 mL of MeOH was added. The reaction mixture was degassed twice more and heated under reflux for 30 min. It was cooled and acidified with about 15 mL of 50% H$_2$O/HOAc. The product was extracted with Et$_2$O (2×50 mL). The Et$_2$O extracts were washed with brine, dried (Na$_2$SO$_4$), and evaporated to give a light yellow solid, which was recrystallized from EtOAc/hexane to give 0.54 g (75% yield) of pale yellow crystals: mp 173°–174° C.; LC (Radialpak A, reverse phase, 50% H$_2$O/MeCN, 2 mL/min, 260 nm) t$_R$ 1.4 min (100%); IR (mull) 2800–3200 (broad, COOH), 1700, 1620, 1310, 1220, 980, 920, 900, 820, 760 cm$^{-1}$; $^1$H NMR (CDCl$_3$/Me$_2$SO-d$_6$) δ1.11 (s, 6, 16$_R$, 17$_R$ CH$_3$), 1.5–1.6 and 1.6–1.7 (2m, 4, 2$_R$,3$_R$ CH$_2$), 1.81 (s, 3, 18$_R$ CH$_3$), 2.0–2.1 (m, 2, 4$_R$ CH$_2$), 6.54 (d, J=16 Hz, 1, 8$_R$ C═CH), 6.90 (d, J=16 Hz, 1, 7$_R$ CH═C), 7.73 (d, J=8.5 Hz, 1, 4'H), 7.77 (s, 1, 5'H), 7.86 and 7.93 (2d, J=8.5 Hz, 2, 7', 8'H), 8.10 (d, J=8.5 Hz, 3'H), 8.67 (s, 1, 1'H); $^{13}$C NMR (CDCl$_3$/MeSO-d$_6$) 18.7 (3$_R$), 21.4 (18$_R$), 28.7 (16$_R$,17$_R$), 32.5 (4$_R$), 33.8 (1$_R$), 39.1 (2$_R$), 124.2, 124.9, 125.5, 127.9, 128.9, 129.4, 129.6, 130.1, 131.4, 131.9, 135.3, 137.0, 137.3, 167.3 ppm (CO$_2$H); UV (EtOH) λ$_{max}$ 317 nm (ε2.41×10$^4$), 254 nm (ε2.71×10$^4$), MS calcd for C$_{22}$H$_{24}$O$_2$ 320.1776, found 320.1786.

EXAMPLE 4

Preparation of (E)-1-(5-Carbethoxy-2-furanyl)-2-methyl-4-(2,6,6-trimethyl-1-cyclohexen-1-yl)-1,3-butadiene

2-Furfuraldiethylacetal

A mixture of 96 g (1.0 mol) of 2-furfural, 177.8 g (1.2 mol) of (EtO)$_3$CH and 4 g of NH$_4$Cl in 50 mL of warm EtOH was heated under reflux for 16 h. The cooled mixture was decanted and fractionally distilled over 2 g of anhydrous Na$_2$CO$_3$. A total of 160 g (94% yield) of the acetal was obtained as a colorless liquid, bp 72°–74° C. (16 min), 81°–83° C. (23 mm); IR (film) 3000, 2900, 1610, 1510, 1460, 1400, 1340, 1240, 1160, 1120, 1060, 1010, 960, 910, 890, 860, 810, 750 cm$^{-1}$; $^1$H NMR (CDCl$_3$) δ1.23 (t, J=7 Hz, 6, CH$_2$CH$_3$), 3.67 (q, J=7 Hz, 4, CH$_2$CH$_3$), 5.60 (s, 1, CH(OCH$_2$CH$_3$)$_2$), 6.3–6.5 (m, 2, HC═CH), 7.4–7.6 (m, 1, C═CH).

2-Carbethoxy-5-furaldehyde

To a solution of 17.0 g (0.1 mol) of 2-furfuraldiethylacetal in 300 mL of anhydrous Et$_2$O at −15° C. was added 67 mL of a 1.5M solution of n-BuLi (0.1 mol) in hexane over a period of 30 min, while the temperature of the reaction mixture was maintained between −10° C. and −15° C. The reaction mixture was gradually raised to room temperature over a period of 1 h, and then gaseous CO$_2$ was bubbled through for 4 h. Dilute HCl (200 mL) was next added, and the mixture was heated under reflux for 1 h. The ethereal layer was separated, and the aqueous phase was washed with 100 mL of EtOAc. The combined organic phase was washed with brine (2×100 mL), dried (Na$_2$SO$_4$), and concentrated to give 8.0 g of a dark-colored solid. This solid was dissolved in 100 mL of anhydrous Me$_2$SO and then stirred at room temperature with 15 g (0.11 mol) of K$_2$CO$_3$ and 8 mL (0.1 mol) of EtI for 60 h. The reaction mixture was diluted with 500 mL of brine and extracted with EtOAc (3×100 mL). The extract was dried (Na$_2$SO$_4$) and concentrated to give 10.0 g of a dark oil, which was eluted through 180 g of silica gel (50% EtOAc/hexane) to give 6.2 g of a brown oil, which was again purified on 150 g of silica gel (25% Et$_2$O/hexane) to give 5.8 g of a yellow solid. The solid was recrystallized from Et$_2$O/hexane to give 5.0 g of the product aldehyde as white needles (30% overall yield), mp 39°–40° C.; IR (mull) 1740, 1700, 1590, 1520, 1420, 1320, 1270, 1230, 1160, 1030, 980, 880, 850, 780 cm$^{-1}$; $^1$H NMR (CDCl$_3$) δ1.35 (t, J=7 Hz, 3, CO$_2$CH$_2$C$\underline{H}_3$), 2.73 (q, J=7 Hz, 2, CO$_2$C$\underline{H}_2$CH$_3$), 7.27 (s, 2, HC=C$\underline{H}$), 9.80 (s, 1, CHO); MS calcd for C$_8$H$_8$O$_4$ 168.0423, found 168.0432.

1-(5-Carbethoxy-2-furanyl)-2-methyl-1-propene

To a suspension of 24.2 g (0.056 mol) of isopropyltriphenylphosphonium iodide in 300 mL of THF at −20° C. was added 37.3 mL of a 1.5M solution of n-BuLi (0.056 mol) in hexane over a 20-min period. The dark brown solution was warmed to 0° C. and maintained at this temperature for 30 min, when almost all of the solid phosphonium salt had disappeared. A solution of 9.42 g (0.056 mol) of 2-carbethoxy-5-furaldehyde in 20 mL of THF was added over a period of 10 min. The resulting clear yellow solution was stirred at room temperature for 20 h and at 50°–60° C. for 1 h. The mixture was diluted with 500 mL of brine and 300 mL of Et$_2$O. The organic layer was washed twice with 300 mL of brine, dried (Na$_2$SO$_4$), and evaporated to afford 11.0 g of the crude product, which was purified on 150 g of SiO$_2$ (12.5% Et$_2$O/hexane) to give 9.0 g of the pure product as a very pale yellow oil: IR (film) 2990, 2950, 1720, 1670, 1590, 1510, 1460, 1380, 1350, 1320, 1270, 1230, 1190, 1160, 1140, 1030, 980, 850, 800, 760 cm$^{-1}$; $^1$H NMR (CDCl$_3$) δ1.25 (t, J=7 Hz, 3, CO$_2$CH$_2$C$\underline{H}_3$), 6.05 (s, 1, C=CH), 6.17 (d, J=4 Hz, 1, 3′H), 7.07 (d, J=4 Hz, 1, 4′H); MS calcd for C$_{11}$H$_{14}$O$_3$ 194.0943, found 194.0946.

3-(5-Carbethoxy-2-furanyl)-2-methyl-2-propenal

A mixture of 8.2 g (0.042 mol) of 1-(5-carbethoxy-2-furanyl)-2-methyl-1-propene, 10.0 g of SeO$_2$ (0.09 mol) and 120 mL of dioxane was degassed three times under argon and heated at 90° C. for 1.5 h. The reaction mixture was cooled, filtered through Celite and evaporated to remove most of the dioxane. The residue was filtered again and washed with 50 mL of dioxane. The filtrate and washings were concentrated to a small volume and chromatographed on 170 g of silica gel (25% Et$_2$O/hexane) to give 3.9 g (44% yield) of a white solid. Recrystallization from EtOAc/hexane gave long white needles, mp 83° C.; IR (mull) 1740, 1690, 1650, 1320, 1280, 1240, 1200, 1040, 980, 780 cm$^{-1}$; $^1$H NMR (CDCl$_3$) δ1.43 (t, J=7 Hz, 3, CH$_2$C$\underline{H}_3$), 2.18 (s, 3, C=CCH$_3$), 4.48 (q, J=7 Hz, 2, C$\underline{H}_2$CH$_3$), 6.88 and 7.35 (2d, J=4 Hz, 2, 3′, 4′H), 7.15 (s, 1, C=CH), 9.60 (s, 1, CHO); MS calcd for C$_{11}$H$_{12}$O$_4$ 208.0736, found 208.0728.

(E)-1-(5-Carbethoxy-2-furanyl)-2-methyl-4-(2,6,6-trimethyl-1-cyclohexen-1-yl)-1,3-butadiene A suspension of 8.87 g (0.019 mol) of β-cyclogeranyltriphenylphosphonium bromide in 200 mL of THF was cooled to −20° C. A solution of 12.3 mL of 1.5M n-BuLi (0.019 mol) in hexane was added over a period of 10 min. When the addition was complete, the mixture was stirred over a period of 10 min. To the resulting deep brown solution was added a solution of 3.85 g (0.019 mol) of 3-(5-carbethoxy-2-furanyl)-2-methyl-2-propenal in 10 mL of THF (5-mL THF rinse). The mixture was stirred overnight at room temperature and for 1 h at 50°–60° C. The clear yellow reaction mixture was concentrated to about 20 mL. Et$_2$O (200 mL) was added. The precipitated triphenylphosphine oxide was removed by filtration through Celite. The filtrate upon evaporation gave 6.5 g of a yellow oil, which was purified on 100 g of silica gel (10% Et$_2$O/hexane) to give 5.3 g (83% yield) of the product as a bright yellow oil. Analytical LC (1% Et$_2$O/hexane, Radialpak B, 2 mL/min, 260 nm) indicated one major and three minor peaks: t$_R$ 13.0 (0.7%), 13.8 (4.3%), 15.6 (93.2%) and 19.0 min (1.8%). Further purification on preparative LC (0.8% Et$_2$O/hexane and 2% EtOAc/hexane) gave 2.9 g of the pure product as a light yellow oil: LC (Radialpak B, 1% Et$_2$O/hexane, 2 mL/min, 260 nm), t$_R$ 15.6 min (100%), reverse phase LC (Radialpak A, 20% H$_2$O/CH$_3$CN, 2 mL/min, 260 nm) t$_R$ 10.74 min (100%); IR (film) 2950, 1720, 1580, 1500, 1380, 1310, 1230, 1190, 1140, 1030, 980, 880, 810, 770 cm$^{-1}$; $^1$H NMR (CDCl$_3$) δ1.05 (s, 6, 16$_R$, 17$_R$ CH$_3$), 1.37 (t, J=7 Hz, 3, CH$_2$CH$_3$), 1.4–1.8 (m, 4, 2$_R$, 3$_R$ CH$_2$), 1.72 (s, 3, 18$_R$, CH$_3$), 2.2$\overline{2}$ (s, 3, 19$_R$ CH$_3$), 4.37 (q, J=7 Hz, 2, C$\underline{H}_2$CH$_3$), 6.25 (s, 1, 10$_R$ C=CH), 6.32 (s, 2, 7$_R$, 8$_R$ HC=CH), 6.42 (d, J=4 Hz, 1, 3′H), 7.22 (d, J=4 Hz, 1, 4′H); $^{13}$C NMR (CDCl$_3$) 14,1, 14.3 (9$_R$, OCH$_2$CH$_3$), 19.2 (3$_R$), 21.6 (18$_R$), 28.9 (16$_R$, 17$_R$), 33.0 (4$_R$), 34.2 (1$_R$), 39.5 (2$_R$), 60.6 (OCH$_2$), 110.8, 116.8, 119.4 (10$_R$, 3′, 4′), 129.2, 129.9 (5$_R$, 7$_R$), 137.0 (8$_R$), 137.4 (6$_R$); 138.9 (9$_R$), 142.8, 157.1 (2′, 5′), 158.7 ppm (C=O); UV (EtOH) λ$_{max}$ 339 nm (ε3.17×10$^4$); MS calcd for C$_{21}$H$_{28}$O$_3$ 328.2038, found 328.2041.

EXAMPLE 5

Preparation of (E)-1-(5-carboxy-2-furanyl)-2-methyl-4-(2,6,6-trimethyl-1-cyclohexen-1-yl)-1,3-butadiene A solution of 1.2 g (21.4 mmol) of KOH in 3 mL of H$_2$O and 5 mL of EtOH was degassed three times and added to a suspension of 1.8 g (5.49 mmol) of the ester of Example 4 in 5 mL of EtOH. The mixture was degassed three timed and heated at 80° C. for 30 min. The cooled solution was then acidified with 12 mL of 50% HOAc and extracted with Et$_2$O. The ethereal layer was washed with brine (2×50 mL), dried (Na$_2$SO$_4$), and concentrated to give 1.6 g of a yellow gel (97% yield), which gradually solidified upon trituration with hexane. Recrystallization from EtOAc and hexane yielded 1.1 g (67% yield) of bright yellow crystals, mp 109° C.; reverse phase LC (Radialpak A, 20% H$_2$O/CH$_3$CN, 2 mL/min, 260 nm) t$_R$ 3.59 min (100%); IR (mull) 1690, 1590, 1510, 1320, 1280, 1240, 1190, 1170, 1050, 980, 770, 740 cm$^{-1}$; $^1$H NMR (CDCl$_3$) δ1.05 (s, 6, 16$_R$, 17$_R$ CH$_3$), 1.4–1.7 (m, 4, 2$_R$, 3$_R$ CH$_2$), 1.73 (s, 3, 18$_R$ CH$_3$), 1.9–2.2 (m, 2, 4$_R$ CH$_2$), 2.27 (s, 3, 19$_R$ CH$_3$), 6.27 (s, 1, 10$_R$ C=CH), 6.32 (s, 2, 7$_R$, 8$_R$ HC=CH), 6.47 (d, J=4 Hz, 1, 3′H), 7.35 (d, J=4 Hz, 1, 4′H), 11.58 (s, 1, CO$_2$H); $^{13}$C NMR (CDCl$_3$) 14.2 (19$_R$), 19.2 (3$_R$), 21.7 (18$_R$), 28.9 (16$_R$, 17$_R$), 33.0 (4$_R$), 34.2 (1$_R$), 39.5 (2$_R$), 111.2, 116.6 121.9 (10, 3′, 4′), 129.8, 130.1 (5$_R$, 7$_R$), 136.9 (8$_R$), 137.4 (6$_R$), 139.9 (9$_R$), 141.8, 158.4 (2′, 5′), 163.8 ppm (C=O);

UV (EtOH) $\lambda_{max}$ 335 nm ($\epsilon 3.66 \times 10^4$); MS calcd for $C_{19}H_{24}O_3$ 300.1725, found 300.1737.

EXAMPLE 6

Preparation of
(E)-1-(5-carbethoxythien-2-yl)-2-methyl-4-(2,6,6-trimethyl-1-cyclohexen-1-yl)-1,3-butadiene

2-Thiophenecarboxaldehydediethylacetal

To a mixture of 64 g (0.57 mol) of 2-thiophenecarboxaldehyde and 120 mL (0.72 mol) of (EtO)$_3$CH was added a warm solution of 2 g of NH$_4$NO$_3$ in 50 mL of absolute EtOH. The mixture was mechanically stirred at 80° C. for 16 h and then was cooled and filtered. The filtrate was distilled from 2 g of anhydrous Na$_2$CO$_3$. The first fraction (15 g) boiling at 30°-40° C. (0.6 mm) was largely (EtO)$_3$CH. The acetal (100 g, 94%) distilled at 64° C. (1.0 mm) as a colorless liquid: IR (film) 2950, 2900, 2850, 1540, 1490, 1430, 1370, 1350, 1310, 1230, 1180, 1150, 1060, 1000, 900, 860, 840, 700 cm$^{-1}$; $^1$H NMR (CDCl$_3$) $\delta$1.23 (t, J=7 Hz, 6, CH$_2$CH$_3$), 3.61 (q, J=7 Hz, 4, CH$_2$CH$_3$), 5.70 (s, 1, CH), 6.8-7.3 (m, 3, C=CH).

2-Carbethoxy-5-thiophenecarboxaldehyde

A solution of 50 g (0.27 mol) of thiophene-2-carboxaldehydediethylacetal in 200 mL of Et$_2$O under argon was treated at room temperature over a 30-min period with 180 mL (0.27 mol) of a 1.47M solution of n-BuLi in hexane. When the addition was complete, the dark brown mixture was stirred for 1 h at room temperature. It was then added over a 45-min period to a slurry of 1 Kg of solid CO$_2$ in 250 mL of dry THF, which was cooled in a dry ice/acetone bath. The mechanically stirred reaction mixture was allowed to warm to room temperature over 4 h and was left to stand for 16 h. The mixture was diluted with 200 mL of H$_2$O before 300 mL of 3N HCl was added. The mixture was heated under reflux for 15 min. The cooled mixture was extracted with Et$_2$O (2$\times$150 mL). The Et$_2$O layer was washed with brine (2$\times$400 mL), dried (Na$_2$SO$_4$), and concentrated to give 30 g of a dark brown oil. TLC (25% Et$_2$O/hexane) indicated the presence of an appreciable amount of 2-thiophenecarboxaldehyde in addition to the desired 2-formyl-5-thiophenecarboxylic acid. A sample was partially purified on silica gel (50% EtOAc/hexane) to give a light yellow solid: $^1$H NMR (Me$_2$SO-d$_6$/CDCl$_3$) $\delta$7.7-8.0 (m, 2, C=CH), 9.9 (broad s, 1, CO$_2$H), 10.03 (s, 1, CHO).

To the crude acid (29 g) dissolved in 200 mL of dry Me$_2$SO were added 30 g (0.22 mol) of anhydrous K$_2$CO$_3$ and 25 mL (0.31 mol) of EtI. The mixture was stirred at room temperature for 20 h. Water (200 mL) was added, and the product was extracted with Et$_2$O (3$\times$150 mL). The ethereal layer was washed with brine (2$\times$250 mL), dried (MgSO$_4$), and concentrated to give a dark brown oil, which was chromatographed on 400 g of silica gel (15% EtOAc/hexane). Unreacted 2-thiophenecarboxaldehyde (10 g) eluted first, followed by 14 g of a mixture of it and the ester. This mixture was purified on preparative LC (4% EtOAc/hexane) to give 12 g (24% yield from the acetal) of the ester as a yellow solid. The ester was recrystallized from EtOAc/hexane to give pale yellow needles, mp 56°-56.5° C.: IR (mull) 1720, 1690, 1540, 1290, 1200, 1100, 1040, 825, 750 cm$^{-1}$; $^1$H NMR (CDCl$_3$) $\delta$1.42 (t, J=7.5 Hz, 3, CH$_2$CH$_3$), 4.39 (q, J=7.5 Hz, 2, CH$_2$CH$_3$), 7.70, 7.81 (2d, J=3.5 Hz, 2, ArH), 9.95 (s, 1, CHO).

(E)-1-(5-Carbethoxythien-2-yl)-2-methyl-4-(2,6,6-trimethyl-1-cyclohexen-1-yl)-1,3-butadiene To a suspension of 3.5 g (6.74 mmol) of (E)-1-(2,6,6-trimethyl-1-cyclohexen-1-yl)-1-buten-3-yltriphenylphosphonium bromide ($\beta$-ionyltriphenylphosphonium bromide) in 30 mL of THF cooled to $-78°$ C. was added over a 5-min period 4.46 mL (6.73 mmol) of a 1.51M solution of n-BuLi in hexane. The mixture was gradually warmed to room temperature and stirred for another 15 min. A solution of 1.24 g (6.74 mmol) of the aldehyde in 6 mL of THF (4 mL THF rinse) was added. The mixture was stirred at room temperature for 16 h and at 50° C. for 1 h. Water (50 mL) was added to the mixture, which was then extracted with 50% Et$_2$O/hexane (4$\times$50 mL). The organic layer was washed with brine (2$\times$100 mL), dried (MgSO$_4$), and concentrated to give a yellow oil, which was passed over a precolumn of 150 g of silica gel (5% EtOAc/hexane) to give 1.70 g (73% yield) of a bright yellow oil. Analytical LC (Radialpak B, 1% Et$_2$O/hexane, 2 mL/min, 260 nm) indicated 2 isomers: t$_R$ 9.6 (68%), 10.04 min (32%). These isomers were separated by multiple passes on preparative LC (0.25% Et$_2$O/hexane) to give 0.6 g (26% yield) of the 1Z,3E isomer and 0.3 g (13% yield) of the all E isomer as bright yellow oils. All E isomer: LC (Radialpak B, 0.5% Et$_2$O/hexane, 2 mL/min, 260 nm) t$_R$ 17.9 min (100%); LC (Radialpak A, 5% H$_2$O/MeOH, 2 mL/min, 260 nm) t$_R$ 5.6 (99%), 6.6 min (1%); IR (film) 2950, 1720, 1450, 1280, 1230, 1100, 960, 750 cm$^{-1}$; 360 MHz $^1$H NMR (CDCl$_3$) $\delta$1.04 (s, 6, 16$_R$, 17$_R$ CH$_3$), 1.38 (t, J=7 Hz, 3, CH$_2$CH$_3$), 1.45-1.55 and 1.6-1.7 (2m, 4, 2$_R$, 3$_R$ CH$_2$), 1.73 (s, 3, 18$_R$ CH$_3$), 2.0-2.1 (m, 2, 4$_R$ CH$_2$), 2.19 (S, 3, 19$_R$ CH$_3$), 4.35 (q, J=7 Hz, 2, CH$_2$CH$_3$), 6.18 (d, J=16 Hz, 1, 8$_R$ C=CH), 6.34 (d, J=16 Hz, 1, 7$_R$ C=CH), 6.57 (s, 1, 10$_R$ C=CH), 6.96 (d, J=4 Hz, 1, 3' C=CH), 7.69 (d, J=4 Hz, 1, 4' C=CH); $^{13}$C NMR (CDCl$_3$) 14.4 (CH$_2$CH$_3$, 19$_R$), 19.2 (3$_R$), 21.7 (18$_R$), 28.9 (16$_R$, 17$_R$), 33.0 (4$_R$), 34.2 (1$_R$), 39.6 (2$_R$), 60.9 (CH$_2$CH$_3$), 122.5 (3'), 127.7 (7$_R$), 129.0 (5$_R$, 10$_R$), 133.1, 137.3, 137.5, 137.8, 148.1 (5'), 162.3 ppm (C=O); UV (EtOH) $\lambda_{max}$ 235 nm ($\epsilon 9.2 \times 10^3$), 353 nm ($\epsilon 3.1 \times 10^4$); MS calcd for $C_{21}H_{28}O_2S$ 344.1810, found 344.1820.

EXAMPLE 7

Alternative preparation of
(E)-1-(5-Carbethoxythien-2-yl)-2-methyl-4-(2,6,6-trimethyl-1-cyclohexen-1-yl)-1,3-butadiene

1-(5-Carbethoxythien-2-yl)-2-methyl-1-propene

A suspension of 17.28 g (40 mmol) of isopropyltriphenylphosphonium iodide in 50 mL of dry THF was cooled to $-40°$ C. while 26 mL (40 mmol) of a 1.54M solution of n-BuLi in hexane was added over a 15-min period. The dark brown mixture was warmed to room temperature over 30 min, and then a solution of 7.4 g (40 mmol) of 2-carbethoxy-5-thiophenecarboxaldehyde in 15 mL of THF was added dropwise to the reaction mixture. The deep violet mixture was stirred at room temperature overnight and 55° C. for 1 h. It was poured into 100 mL of ice-water. The product was extracted with Et$_2$O (3$\times$60 mL). The ethereal extracts were washed with brine (2$\times$150 mL), dried (MgSO$_4$), and evaporated to give 14.5 g of a dark brown oil, which was passed through 200 g of silica gel (10% Et$_2$O/hexane) to give 5.66 g (67% yield) of 1-(5-carbethoxythien-2-yl)-2-methyl-1-propene as a pale yellow oil: IR (film) 2950, 1710 (C=O), 1650, 1520, 1450, 1370, 1320, 1270, 1250, 1240, 1170, 1100, 850, 750 cm$^{-1}$; $^1$H NMR (CDCl$_3$) δ1.40 (t, 3, J=7 Hz, CH$_2$CH$_3$), 2.02 and 2.07 (2s, 6, (CH$_3$)$_2$C=C), 4.43 (q, J=7 Hz, 2, CH$_2$CH$_3$), 6.47 (broad s, 1, C=CH), 6.92 (d, J=4 Hz, 1, 3' C=CH), 7.75 (d, J=4 Hz, 1, 4' C=CH).

(E)-3-(5-Carbethoxythien-2-yl)-2-methyl-2-propenal

A mixture of 3.8 g (17.2 mmol) of 1-(5-carbethoxythien-2-yl)-2-methyl-1-propene and 5.0 g (45 mmol) of SeO$_2$ in 60 mL of dioxane and 0.8 mL (44 mmol) of H$_2$O was degassed three times under argon and heated under reflux for 45 min. Cooling, filtration over Celite, and concentration gave 6.8 g of a light-brown solid, which was diluted with 50 mL of Et$_2$O and filtered. The filtrate was concentrated and passed over a column of 150 g of silica gel (15% EtOAc/hexane) to give 2.35 g (60% yield) of the aldehyde as a pale yellow solid, a portion of which was recrystallized from EtOAc/hexane to give white needles, mp 98° C.: IR (mull) 1720, 1680, 1620, 1380, 1290, 1250, 1180, 1160, 1100, 1020, 890, 850, 815, 750 cm$^{-1}$; $^1$H NMR (CDCl$_3$) δ1.42 (t, J=7 Hz, 3, CH$_2$CH$_3$), 2.17 (s, 3, C=CCH$_3$), 4.47 (q, J=7 Hz, 2, CH$_2$CH$_3$), 7.40 (d, J=4 Hz, 1, 3' C=CH), 7.43 (s, 1, C=CH), 7.83 (d, J=4 Hz, 1, 4' C=CH), 9.63 (s, 1, CHO); MS calcd for C$_{11}$H$_{12}$O$_3$S 224.0507, found 224.0519.

(E)-1-(5-Carbethoxythien-2-yl)-2-methyl-4-(2,6,6-trimethyl-1-cyclohexen-1-yl)-1,3-butadiene A suspension of 4.95 g (10.3 mmol) of β-cyclogeranyltriphenylphosphonium bromide in 40 mL of THF was degassed twice under argon and cooled to −78° C. before 6.65 mL (10.2 mmol) of 1.54M n-BuLi in hexane was added over a 10-min period. The mixture was warmed to 0° C. over a 45-min period. Next, a solution of 2.3 g (10.3 mmol) of (E)-3-(5-carbethoxythien-2-yl)-2-methyl-2-propenal in 10 mL of THF (3-mL THF rinse) was added to the reaction mixture over a 10-min period. The mixture was stirred at room temperature for 16 h and at 55°-60° C. for 1 h, and was then cooled, diluted with 100 mL of ice-water and extracted with Et$_2$O (3×50 mL). The Et$_2$O layer was washed with brine (2×100 mL), dried (MgSO$_4$), and evaporated to give 7 g of crude product, which was dissolved in hexane and filtered. The filtrate was concentrated to give 3.8 g of a yellow oil, which was passed over 100 g of silica gel (5% EtOAc/hexane) to give 3.06 g of a yellow oil. Further purification by preparative LC (1% Et$_2$O/hexane) gave 2.0 g (57% yield) of (E)-1-(5-carbethoxythien-2-yl)-2-methyl-4-(2,6,6-trimethyl-1-cyclohexen-1-yl)-1,3-butadiene as a yellow oil, which crystallized on standing, mp 68°-70° C.: LC (Radialpak B, 1% Et$_2$O/hexane, 2 mL/min, 260 nm) t$_R$ 12.2 (2.5%), 12.8 min (97.5%); LC (Radialpak A, 5% H$_2$O/MeOH, 2 mL/min, 260 nm) t$_R$ 4.71 (0.6%), 6.05 (1.1%), 7.26 min (98.3%); 360 MHz $^1$H NMR (CDCl$_3$) δ1.04 (s, 6, 16$_R$, 17$_R$ CH$_3$), 1.38 (t, J=7 Hz, 3, CH$_2$CH$_3$), 1.45-1.55 and 1.6-1.7 (2m, 4, 2$_R$, 3$_R$ CH$_2$), 1.73 (s, 3, 18$_R$ CH$_3$), 2.0-2.1 (m, 2, 4$_R$ CH$_2$), 2.19 (s, 3, 19$_R$ CH$_3$), 4.35 (q, J=7 Hz, 2, CH$_2$CH$_3$), 6.18 (d, J=16 Hz, 1, 8$_R$ C=CH), 6.34 (d, J=16 Hz, 1, 7$_R$ HC=C), 6.57 (s, 1, 10$_R$ C=CH), 6.96 (d, J=4 Hz, 1, 3' C=CH), 7.69 (d, J=4 Hz, 1, 4' C=CH); $^{13}$C NMR (CDCl$_3$) 14.4 (CH$_2$CH$_3$, 19$_R$), 19.3 (3$_R$), 21.7 (18$_R$), 29.0 (16$_R$, 17$_R$), 33.1 (4$_R$), 34.3 (1$_R$), 39.6 (2$_R$), 61.0 (CH$_2$CH$_3$), 122.5 (3'), 127.7 (7$_R$), 129.0 (5$_R$, 10$_R$), 133.1, 137.3, 137.5, 137.8, 148.1 (5'), 162.3 ppm (C=O); UV (EtOH) λ$_{max}$ 237 nm (ε9.4×10$^3$), 353 nm (ε3.2×10$^4$); MS calcd for C$_{21}$H$_{28}$O$_2$S 344.1810, found 344.1814.

EXAMPLE 8

Preparation of (E)-1-(5-carboxythien-2-yl)-2-methyl-4-(2,6,6-trimethyl-1-cyclohexen-1-yl)-1,3-butadiene A solution of 1.0 g (15.1 mmol) of 85% KOH in 3 mL of H$_2$O and 5 mL of EtOH was added to a suspension of 1.8 g (5.23 mmol) of (E)-1-(5-carbethoxythien-2-yl)-2-methyl-4-(2,6,6-trimethyl-1-cyclohexen-1-yl)-1,3-butadiene in 5 mL of EtOH. The mixture was degassed under argon twice and heated at 80° C. for 30 min. The clear yellow solution was cooled and acidified with 12 mL of 50% aqueous HOAc. The precipitated acid was extracted with 100 mL of Et$_2$O, and the Et$_2$O layer was washed with 50 mL of H$_2$O and 50 mL of brine, dried (Na$_2$SO$_4$), and evaporated to give 1.7 g of a bright yellow solid, which was recrystallized from 75 mL of MeOH to give two crops (0.75 g and 0.65 g, 85%) of bright yellow crystals: mp 215°-216° C.; LC (Radialpak A, 20% H$_2$O/MeOH, 2 mL/min, 260 nm) t$_R$ 8.78 min (100%); IR (mull) 1680, (C=O), 1520, 1440, 1380, 1310, 1100, 1030, 970, 880, 810, 750 cm$^{-1}$; 360 MHz $^1$H NMR (Me$_2$SO-d$_6$) δ1.03 (s, 6, 16$_R$, 17$_R$ CH$_3$), 1.4-1.5 and 1.55-1.65 (2m, 4, 2$_R$, 3$_R$ CH$_2$), 1.70 (s, 3, 18$_R$ CH$_3$), 2.0-2.1 (m, 2, 4$_R$ CH$_2$), 2.13 (s, 3, 19$_R$ CH$_3$), 6.24 (d, J=16 Hz, 1, 8$_R$ C=CH), 6.39 (d, J=16 Hz, 1, 7$_R$ HC=C), 6.77 (s, 1, 10$_R$ C=CH), 7.15 (d, J=4 Hz, 1, 3' C=CH), 7.67 (d, J=4 Hz, 1, 4' C=CH); $^{13}$C NMR (Me$_2$SO-d$_6$) 1.43 (19$_R$), 19.0 (3$_R$), 21.7 (18$_R$), 29.0 (16$_R$, 17$_R$), 32.8 (1$_R$, 4$_R$), 39.4 (2$_R$), 122.9 (3'), 128.6 (7$_R$, 10$_R$), 129.5 (5$_R$), 133.2, 137.1, 137.2, 147.2 (5'), 163.1 ppm (C=O); UV (EtOH) λ$_{max}$ 233 nm (ε9.4×10$^3$), 347 nm (ε3.2 10$^4$); MS calcd for C$_{19}$H$_{24}$O$_2$S 316.1497, found 316.1509.

The retinoids of formula (1) may be used topically or systemically as chemopreventive agents and in the treatment, amelioration, or prevention of the skin disorders and rheumatic disorders for which retinoic acid and other retinoids are useful. In this regard, they may be used for therapy in animals, including humans, of premalignant epithelial cell lesions, as a prophylaxis against tumor promotion in epithelial cells and treatment for dermatoses such as icthyoses, follicular disorders, benign epithelial disorders, and other proliferative skin diseases (nonmalignant conditions of the skin that are characterized by epidermal cell proliferation or imcomplete cell differentiation) such as acne, psoriasis, eczema, atopic dermatitis, nonspecific dermatitis and the like. When used for such treatments they will usually be formulated with a pharmaceutically liquid, semi-solid, or solid carrier. A pharmaceutically acceptable carrier is a material that is nontoxic and generally inert and does not affect the functionality of the active ingredients adversely. Such materials are well known and include those materials sometimes referred to as diluents or vehicles in the pharmaceutical formulation art. The carrier may be organic or inorganic in nature. Examples of pharmaceutically acceptable carriers that may be used to formulate the retinoids are water, gelatin, lactose, starch, mineral oil, cocoa butter, dextrose, sucrose, sorbitol, mannitol, gum acacia, alginates, cellulose, talc, magnesium stearate, polyoxyethylene sorbitan monolaurate, and other commonly used pharmaceutical carriers. In addition to the retinoid and carrier the formulation may contain minor amounts of additives such as flavoring agents, coloring agents, thickening or gelling agents, emulsifiers, wetting agents, buffers, stabilizers, and preservatives such as antioxidants.

For topical administration the retinoids are conveniently provided in the form of ointments, tinctures, creams, solutions, lotions, sprays, suspensions, and the like. The amount of retinoid in such topical formulations will normally be in the range of about 0.01 to about 1% by weight. For enteral (oral or rectal) administration the retinoids will typically be formulated as tablets, capsules, dragees, syrups, solutions, or suppositories. For parenteral administration the retinoids will be formulated as injectable solutions or suspensions.

The dosages and dosage regimen in which the retinoids are administered will vary according to, the dosage form, mode of administration, the condition being treated and particulars of the patient being treated. They will, of course, be administered in chemopreventive (tumor promotion inhibiting) amounts or therapeutically effective amounts. For adult humans such chemopreventive amounts will usually be about 0.01 mg to 10.0 mg daily given in one or more doses. Oral doses will generally be less that topical doses and doses for treating skin disorders will typically be less than doses administered for chemoprevention. The dose for treating skin disorders will be on the order of, but normally less than, the dose of retinoic acid prescribed for the disorder.

The usefulness of the invention compounds was demonstrated by testing the compounds of the Examples of the ornithine decarboxylase (ODC) assay, Verma, A. K. and Boutwell, R. K.; Cancer Res (1977) 37:2196–2201, and the tracheal organ culture assay, Newton, D. L.; Henderson, W. R.; and Sporn, M. B.; Cancer Res (1980) 40:3413–3425. The ODC assay measures a compound's ability to prevent the induction of ODC. The tracheal organ culture assay measures a compound's ability to reverse keratinization.

The ODC assay is carried out as follows. Female Charles River CD-1 mice from Charles River Breeding Laboratories, Wilmington, Mass., are used (age 7 to 9 weeks). The dorsal hair of the mice is shaved 1 to 2 days before testing, and only mice showing no hair regrowth are used. A single dose of 12-O-tetradecanoylphorbol-13-acetate (TPA) (10.5 $\mu$g, 17 nmol) in 0.2 mL of acetone is applied topically to the back of each mouse. The test compound, at one of three dose levels (1.7, 17 and 170 nmol), dissolved in 0.2 mL of acetone is applied 1 hour before the TPA treatment to the test groups; the control group is treated with acetone alone. The mice are killed by cervical dislocation five hours after TPA treatment. Determinations are done in triplicate.

The epidermis is obtained from the sacrificed animals. To obtain sufficient material, the dorsal skins from 2 to 3 mice in each treatment group are pooled. The depilatory agent Nudit ® (Helena Rubinstein, New York) is applied to the shaved area of the skin; after 5 minutes, it is washed off thoroughly with cold tap water. Then the skin is excised and plunged immediately into ice-cold water; it is then placed in a 55° C. water bath for 30 seconds and reimmersed in ice-cold water for at lease another 30 seconds. The skin is placed epidermis side up on a cold plate, and the epidermis is scraped off with a razor blade. The pooled epidermal sheets are homogenized (Polytron PT-10 homogenizer) at 0° to 4° C. for 15–20 seconds in 50 mM sodium phosphate and 0.1 mM ethylenediaminetetraacetic acid (EDTA), at a volume of 1 mL/skin.

The supernatant fraction remaining after centrifugation of the homogenate at 10,000$\times$g for 30 seconds at 0° C. is used for the enzyme assay. Enzyme activity is determined using the microassay for ODC as described by Verma and Boutwell to measure the release of $^{14}CO_2$ from DL-[1-$^{14}$C]-ornithine (58 mCi/mmol) after incubation with the 10,000$\times$g supernatant. The incubations are carried out by decanting, with a Pasteur pipette, 100 $\mu$L of the supernatant containing 100 to 120 $\mu$g of protein into two or three 15-mL Corex tubes in a shaking water bath at 37° C. The assay mixture in the tubes consists of 50 $\mu$L of 100 mM sodium phosphate buffer (pH 7.2), 10 $\mu$L of 4 mM pyridoxal phosphate, 40 $\mu$L of 25 mM dithiothreitol, and 1 $\mu$L of 0.1M EDTA. The center wells in the tubes are filled with 200 $\mu$L of a 2:1 solution (v/v) of ethanolamine:2-methoxyethanol. The reaction is started by adding 50 $\mu$L of substrate (0.5 $\mu$Ci of DL-[1-$^{14}$C]-ornithine in 2 mM cold ornithine) at 1-minute intervals by injection to each of the stoppered tubes. Incubations are routinely carried out at 37° C. for 30 to 60 minutes. The reaction is stopped by addition of 0.5 ml of 2M citric acid, and incubation is continued for an additional hour without heating to ensure complete absorption of $^{14}CO_2$.

Radioactivity is measured using a toluene-based scintillant (4 g of PPO and 50 mg of POPOP/L of toluene) in a Beckman LS-250 liquid scintillation counter. Enzyme activity is determined in triplicate and expressed as nanomoles of $CO_2$ released in 30 minutes per milligram of protein. Enzyme activity is linear for the protein concentration used. The protein concentrations of the epidermal extracts are determined by the Lowry procedure, using bovine serum albumin as the standard.

The tracheal organ culture assay is carried out as follows. Tracheas are taken from hamsters that are in very early stages of vitamin A deficiency and placed in organ culture. At the time of culture, the animals are still gaining weight; the tracheal epithelium is generally low columnar or cuboidal, with only occasional patches of squamous metaplasia. Each trachea is opened from the larynx to the carina along the membranous dorsal wall and cultured in a serum-free medium (CMRL-1066; with crystalline bovine insulin, 0.1 $\mu$g/ml; hydrocortisone hemisuccinate, 0.1 $\mu$g/ml; glutamine, 2 mM; penicillin, 100 units/ml; and streptomycin, 100 $\mu$g/ml, added). Cultures are gassed with 50% oxygen, 45% nitrogen, and 5% $CO_2$. The culture dishes are rocked at 35.5–36.0 degrees to allow the tracheas contact with both gas and medium. All tracheas are grown in medium containing no retinoid for the first 3 days. At the end of 3 days, some tracheas are harvested; almost all of these tracheas have significant squamous metaplasia, and approximately 60% have keratinized lesions. The remaining tracheas are then divided into different groups which are treated with either; (1) retinoid dissolved in dimethylsulfoxide (final concentration of DMSO in culture medium is never greater than 0.1%) or (2) an equivalent amount of DMSO alone. Culture medium is changed three times a week, and all of the remaining tracheas are harvested at the end of 10 days in culture. Tracheas are fixed in 10% buffered formalin and embedded in paraffin. Cross sections of five micrometers are made through the mid-portion, stained with hematoxylin and eosin, and then scored with a microscope for the presence of keratin and keratohyaline granules, both of which are found in approximately 90% of control cultures that received no retinoid for the entire 10 day culture period. Retinoids are scored as "inactive" if both keratin and kerato-hyaline granules are seen; they are scored as "active" if neither keratin nor keratohyaline granules are seen, or if keratohyaline granules alone are absent.

The table below gives the results of these tests.

|  | Reversal of Keratinization in Hamster Tracheal Organ Culture | | Inhibition of Induction of Ornithine Decarboxylase by 12-O—Tetradecanoylphorbol-13-acetate in Mouse Skin | |
|---|---|---|---|---|
|  | Conc (M) | Active/Total Cultures (%) | Dose (nmol) | % Inhibition of Control |
| Example 1 | $10^{-8}$ | 15/16 (94) | 17 | 45 |
|  | $10^{-9}$ | 7/14 (50) | 1.7 | 0 |
|  | $10^{-10}$ | 4/14 (28) |  |  |
| Example 3 | $10^{-8}$ | 7/7 (100) | 17 | 48 |
|  | $10^{-9}$ | 7/7 (100) | 1.7 | 30 |
|  | $10^{-10}$ | 3/7 (43) |  |  |
| Example 4 | $10^{-8}$ | 2/7 (29) | 17 | 9 |
|  | $10^{-9}$ | 2/7 (29) | 1.7 | 9 |
|  | $10^{-10}$ | 2/6 (33) |  |  |
| Example 5 | $10^{-8}$ | 3/6 (50) | 17 | 5 |
|  | $10^{-9}$ | 3/7 (43) | 1.7 | 7 |
|  | $10^{-10}$ | 3/7 (43) |  |  |
| Example 6 | $10^{-8}$ | 13/13 (100) | 17 | 77 |
|  | $10^{-9}$ | 10/14 (71) | 1.7 | 67 |
|  | $10^{-10}$ | 6/14 (43) |  |  |
| Example 8 | $10^{-8}$ | 15/15 (100) | 17 | 67 |
|  | $10^{-9}$ | 14/15 (93) | 1.7 | 42 |
|  | $10^{-10}$ | 7/15 (47) |  |  |

These results indicate that the retinoids of the invention possess biological activity that makes them useful as chemopreventive agents and therapeutic agents for treating nonmalignant skin disorders.

Modifications of the above described modes for carrying out the invention that are obvious to those of skill in the fields of organic chemistry, pharmaceuticals, and/or medicine are intended to be within the scope of the following claims.

We claim:

1. A compound of the formula:

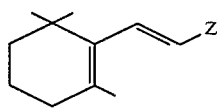

where Z is

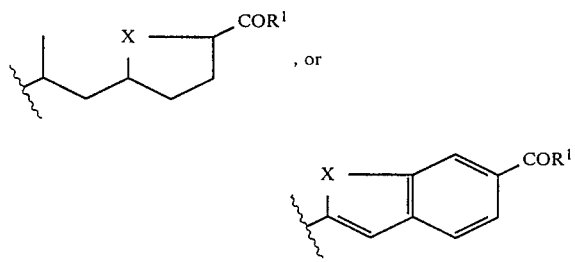

and X is a chalcogen atom of atomic number 8 or 16, $R^1$ is hydroxyl, alkoxy, aroxy, or $NR^2R^3$ where $R^2$ is hydrogen, alkyl, or aryl and $R^3$ is alkyl or aryl.

2. The compound of claim 1 wherein the alkoxy group represented by $R^1$ contains 1 to about 8 carbon atoms, the aroxy group represented by $R^1$ contains 6 to about 15 carbon atoms, the alkyl groups represented by $R^2$ and $R^3$ each contain 1 to about 8 carbon atoms, and the aryl groups represented by $R^2$ and $R^3$ each contains 6 to about 15 carbon atom.

3. The compound of claim 1 wherein the alkoxy group represented by $R^1$ contains 1 to 4 carbon atoms, the aroxy groups represented by $R^1$ are phenoxy, monohydroxyphenoxy, or monoalkoxyphenoxy where the alkoxy group contains 1 to 4 carbon atoms, the alkyl groups represented by $R^2$ and $R^3$ each contains 1 to 4 carbon atoms, and the aryl groups represented by $R^2$ and $R^3$ are pheny, 4-hydroxyphenyl, or 4-methoxyphenyl.

4. The compound of claim 1 where Z is

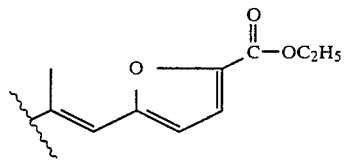 (a)

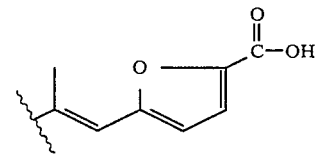 (b)

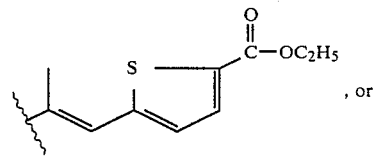 (c)

, or

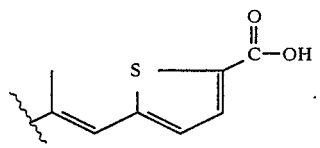 (d)

5. A pharmaceutical composition comprising a pharmaceutically effective amount of the compound of claim 1 combined with a pharmaceutically acceptable carrier.

6. A pharmaceutical composition comprising a pharmaceutically effective amount of the compound of claim 2 combined with a pharmaceutically acceptable carrier.

7. A pharmaceutical composition comprising a pharmaceutically effective amount of the compound of claim 3 combined with a pharmaceutically acceptable carrier.

8. A pharmaceutical composition comprising a pharmaceutically effective amount of the compound of claim 4 combined with a pharmaceutically acceptable carrier.

9. A method of inhibiting tumor promotion in epithelial cells of a living animal comprising administering a tumor promotion inhibiting amount of the compound of claim 1 to the animal.

10. A method of inhibiting tumor promotion in epithelial cells of a living animal comprising administering a tumor promotion inhibiting amount of the compound of claim 2 to the animal.

11. A method of inhibiting tumor promotion in epithelial cells of a living animal comprising administering a tumor promotion inhibiting amount of the compound of claim 3 to the animal.

12. A method of inhibiting tumor promotion in epithelial cells of a living animal comprising administering a tumor promotion inhibiting amount of the compound of claim 4 to the animal.

13. The method of claim 9 wherein the animals is a human.

14. A method of treating a living animal for a non-malignant skin disorder comprising administering a therapeutically effective amount of the compound of claim 1 to the animal.

15. A method of treating a living animal for a non-malignant skin disorder comprising administering a therapeutically effective amount of the compound of claim 2 to the animal.

16. A method of treating a living animal for a non-malignant skin disorder comprising administering a therapeutically effective amount of the compound of claim 3 to the animal.

17. A method of treating a living animal for a non-malignant skin disorder comprising administering a therapeutically effective amount of the compound of claim 4 to the animal.

18. The method of claim 14 wherein the compound is administered topically to the affected area of skin.

19. The method of claim 14 wherein the compound is administered orally to the animal.

20. The method of claim 14 wherein the animal is a human.

* * * * *